(12) United States Patent
Hamamatsu et al.

(10) Patent No.: US 7,741,527 B2
(45) Date of Patent: Jun. 22, 2010

(54) SOLID PHOSPHORIC ACID CATALYST AND METHOD FOR DIMERIZATION OF OLEFIN USING THE SAME

(75) Inventors: Tatsuo Hamamatsu, Yokohama (JP);
Nobuhiro Kimura, Yokohama (JP);
Tsutomu Takashima, Yokohama (JP);
Takashi Morikita, Yokohama (JP)

(73) Assignee: Nippon Oil Corporation, Tokyo (JP)

( * ) Notice: Subject to any disclaimer, the term of this patent is extended or adjusted under 35 U.S.C. 154(b) by 616 days.

(21) Appl. No.: 11/632,369

(22) PCT Filed: Jul. 13, 2005

(86) PCT No.: PCT/JP2005/013427
§ 371 (c)(1),
(2), (4) Date: Jan. 12, 2007

(87) PCT Pub. No.: WO2006/009229
PCT Pub. Date: Jan. 26, 2006

(65) Prior Publication Data
US 2008/0027261 A1    Jan. 31, 2008

(30) Foreign Application Priority Data
Jul. 16, 2004   (JP) .............................. 2004-210743
May 25, 2005   (JP) .............................. 2005-152696

(51) Int. Cl.
*C07C 2/24* (2006.01)
*B01J 27/14* (2006.01)
(52) U.S. Cl. ...................................... 585/514; 502/208
(58) Field of Classification Search ................. 585/514; 502/208
See application file for complete search history.

(56) References Cited

U.S. PATENT DOCUMENTS

| 3,661,801 A | 5/1972 | Gutmann et al. |
| 3,673,111 A | 6/1972 | Hovarth et al. |
| 6,040,262 A | 3/2000 | Fougret et al. |
| 6,689,927 B1 * | 2/2004 | Frame et al. ................ 585/510 |

FOREIGN PATENT DOCUMENTS

| CN | 1187388 A | 7/1998 |
| CN | 1328877 A | 1/2002 |
| CN | 1483717 A | 3/2004 |
| JP | 47-2863 | 2/1972 |
| JP | 47-29292 | 11/1972 |
| JP | 52-26389 | 2/1977 |
| JP | 11-314040 | 11/1999 |
| JP | 2001-199907 | 7/2001 |

* cited by examiner

*Primary Examiner*—In Suk Bullock
(74) *Attorney, Agent, or Firm*—Weingarten, Schurgin, Gagnebin & Lebovici LLP

(57) ABSTRACT

The present invention provides a solid phosphoric acid catalyst which attains high activity and dimer selectivity in olefin dimerization reaction and an efficient method for dimerization of olefin using the same. The solid phosphoric acid catalyst comprises phosphoric acid supported on a siliceous carrier, the proportion of orthophosphoric acid in the phosphoric acid supported being 60 mol % or more in terms of phosphorus atom amount. The solid phosphoric acid catalyst is prepared by bringing a phosphoric acid aqueous solution into contact with the siliceous carrier followed by drying, the preparation step being carried out at a temperature lower than 100° C. Also provided is a method for bringing an olefin-containing raw material into contact with the catalyst. In this method, the olefin-containing raw material contains water in an amount of 10 to 1000 mass ppm, the olefin-containing raw material is brought into contact with the solid phosphoric acid catalyst in a liquid phase, and the olefin is a monoolefin having 3 to 7 carbon atoms.

10 Claims, No Drawings

SOLID PHOSPHORIC ACID CATALYST AND METHOD FOR DIMERIZATION OF OLEFIN USING THE SAME

This application is a §371 national phase filing of PCT/JP2005/013427 filed Jul. 13, 2005, and claims priority to Japanese application No. 2004-210743 filed Jul. 16, 2004 and to Japanese application No. 2005-152696 filed May 25, 2005.

TECHNICAL FIELD

The present invention relates to a solid phosphoric acid catalyst comprising phosphoric acid supported on a carrier, and a method for selective dimerization of olefin using the same.

BACKGROUND ART

Oligomers of olefin are used for various purposes and, particularly, dimers of low-molecular-weight olefin (e.g., propylene, n-butene, isobutene, pentene, etc.) are important as high-octane number base materials for gasoline production, or important as chemical intermediate raw materials. Oligomerization including olefin dimerization is carried out using acid catalysts, and many studies have been made therefor. Conventional examples of the acid catalyst include sulfuric acid, hydrogen fluoride, phosphoric acid, aluminum chloride, boron fluoride, amorphous or crystalline aluminosilicate, clay, ion-exchange resin, mixed oxide, and solid acid such as an acid supported on solid carrier, and various examinations have been made also for the solid phosphoric acid catalyst which provide inexpensive and simplified chemical manufacturing processes.

There are disclosed to oligomerize propylene using a solid phosphoric acid prepared in a calcination condition of 100° C. or higher (Patent Literature 1) and to oligomerize propylene using a catalyst prepared by crystallizing an amorphous mixture of phosphoric acid and a siliceous raw material in conditions of 250-450° C. and water vapor concentration of 3-50 mol % (a catalyst consisting of silicon orthophosphate and silicon pyrophosphate) (Patent Literature 2).

It is hitherto known that the condensation degree of phosphoric acid in the solid phosphoric acid catalyst affects the activity of oligomerization reaction of olefin, and there also are disclosed examples of oligomerization of olefins of C3, C4 and the like using a catalyst in which the mass ratio of a free phosphoric acid component which is eluted when the solid phosphoric acid catalyst is dipped in water (non-condensed or low-condensed phosphoric acid such as orthophosphoric acid or pyrophosphoric acid) to the catalyst is small (the proportion of orthophosphoric acid in the phosphoric acid supported is about 46 mol % at most in terms of phosphorus atom amount) (Patent Literature 3 and Non-Patent Literature 1).

However, not only the oligomerization of olefin using the above-mentioned conventional phosphoric acid catalysts is not mainly intended for dimerization of olefin, but also the use of the conventional solid phosphoric acid catalysts unavoidably involves by-production of high polymerized products of olefin, and it was thus difficult to selectively provide dimers of olefin.

In a phosphoric acid aqueous solution supporting operation, though affected by operating condition such as operating time or temperature, condensation of the supported orthophosphoric acid in drying process is easy to proceed. Even after once supported, the condensation easily proceeds in the same manner. As described later, particularly, a low orthophosphoric acid concentration in the total phosphoric acid facilitates the proceed of the condensation. As described in Patent Literature 3, also, a highly-condensed phosphoric acid which is once condensed is dissolved only very slowly to water (Patent Literature 3, the latter part of Paragraph 0036). Namely, the progress of hydrolysis of the highly-condensed phosphoric acid is virtually slow.

In other words, in the conventional phosphoric acid aqueous solution supporting operation, the condensation is consequently easy to proceed due to the low orthophosphoric acid concentration in the total phosphoric acid or the like, and the supported amount of highly-condensed phosphoric acid must be increased. Therefore, in the above-mentioned case (the proportion of orthophosphoric acid in the phosphoric acid supported being about 46 mol % at most in terms of phosphorus atom amount), the actual proportion of orthophosphoric acid is predicted to be far less than the maximum value as a theoretic value (about 46 mol %) because the condensation progresses even if the orthophosphoric acid is produced. It is not easy for the highly-condensed phosphoric acid which is once condensed and supported in the drying process to return to orthophosphoric acid even if it is thereafter hydrolyzed by contact with liquefied or gaseous water in a reaction system. Further, in the supported orthophosphoric acid, the condensation of orthophosphoric acid can proceed depending on the reaction condition even if the orthophosphoric acid concentration in the total phosphoric acid is high, as well as being low.

Patent Literature 1: Japanese Patent Examined Publication No. 8-29251

Patent Literature 2: Japanese Patent Examined Publication No. 7-59301

Patent Literature 3: Japanese Patent Laid Open No. 2001-199907

Non-Patent Literature 1: "Applied Catalysis A: General", 1993, 97, p. 177-196

DISCLOSURE OF THE INVENTION

The present invention provides solid phosphoric acid catalyst which shows high activity and dimer selectivity in olefin dimerization reaction, and an efficient method for dimerization of olefin.

According to a first aspect of the present invention, the solid phosphoric acid catalyst comprises phosphoric acid (including those which can change to phosphoric acid by hydrolysis, hereinafter the same as above) supported on carrier, the proportion of orthophosphoric acid in the phosphoric acid supported being 60 mol % or more in terms of phosphorus atom amount.

According to a second aspect of the invention, the solid phosphoric acid catalyst according to the first aspect is prepared by bringing a phosphoric acid aqueous solution into contact with the carrier followed by drying, the preparation process being carried out at a temperature lower than 100° C.

According to a third aspect of the invention, the method for dimerization of olefin comprises bringing olefin-containing raw material into contact with the solid phosphoric acid catalyst according to the first or second aspect.

According to a fourth aspect of the invention, in the method according to the third aspect, the olefin-containing raw material contains water in an amount of 10 to 1000 mass ppm.

According to a fifth aspect of the invention, in the method according to the third or fourth aspect, the olefin-containing raw material is brought into contact with the solid phosphoric acid catalyst in liquid phase.

According to a sixth aspect of the invention, in the method according to any one of the third to fifth aspects, the olefin is C3-C7 monoolefin.

EFFECT OF THE INVENTION

The solid phosphoric acid catalyst of the present invention is particularly suitable for olefin dimerization reactions, and enables efficient production of olefin dimers because it has high activity and dimer selectivity in the reactions and an extended catalytic life.

BEST MODE FOR CARRYING OUT THE INVENTION

The present invention will be described further in detail.

As the carrier of the solid phosphoric acid catalyst used in the present invention, any carrier which can support phosphoric acids can be used without limitation, preferably, including molded products of siliceous supports such as diatomite, infusorial earth, ciliate earth, kieselguhr, kaolin, fuller's earth, and artificial porous silica and mixtures thereof. In the molding process of the carrier, calcination can be performed in any temperature condition for the purpose of giving sufficient strength, pore capacity, and specific surface area. The molding method and the shape of molded product are not particularly limited and, for example, various molded products of granular, sheet-like or pellet-like shapes can be formed, for example, by means of tableting, extrusion molding, spray drying, rolling pelletization, or oil pelletization, with a grain size being about 0.5 to 5 mm.

Concrete examples of the phosphoric acid include orthophosphoric acid and condensates thereof (pyrophosphoric acid, polyphosphoric acid, etc.). In the supporting operation, those which can change to phosphoric acid by hydrolysis (phosphoric acid precursors), e.g., phosphoric acid esters of C1 to C8 alcohols can be also used. Mixtures thereof are also usable.

The ratio of phosphoric acid to the carrier in the catalyst (the phosphoric acid being calculated as orthophosphoric acid, or phosphoric acids other than orthophosphoric acid being converted to the amount of orthophosphoric acid produced when perfectly hydrolyzed; hereinafter referred to as "phosphoric acid support amount") is 10 to 200 mass %, preferably 30 to 120 mass %. A smaller support amount causes low activity in olefin dimerization reaction, while a larger support amount increases elution of the phosphoric acid to the reaction solution, causing undesirable corrosion of equipment and devices.

In the present invention, the proportion of orthophosphoric acid to other condensed polyphosphoric acids and the like in the phosphoric acid supported on the carrier is important. Namely, when the proportion of orthophosphoric acid in the phosphoric acid is 60 mol % or more, preferably 70 mol % or more, more preferably 80 mol % or more in terms of phosphorus atom amount, excellent activity and dimer selectivity can be provided in the olefin dimerization reaction.

Although the progress of the condensation of orthophosphoric acid is extremely slowed when the proportion of orthophosphoric acid in the phosphoric acid is 60 mol % or more in terms of phosphorus atom amount, the condensation of orthophosphoric acid shows rapid progress, causing sudden deterioration of the activity in olefin dimerization reaction when the proportion is smaller than 60 mol %. For maintaining high activity and dimer selectivity in olefin dimerization reaction for a long period, it is important to bring olefin into contact with the catalyst in a state where the proportion of orthophosphoric acid in the phosphoric acid in the catalyst is 60 mol % or more.

The means for measuring the proportion of orthophosphoric acid in the phosphoric acid in the catalyst is not particularly limited, but solid nuclear magnetic resonance spectroscopy of phosphorus nucleus ($^{31}P$) is most suitable method therefor. The chemical shift values of phosphorus nuclei of phosphoric acids are shifted to the higher magnetic field according to the condensation degree, and when the shift value of orthophosphoric acid is set as 0 ppm, the shift value of pyrophosphoric acid and polyphosphoric acid are observed at about −11.8 ppm and at about −24.3 ppm, respectively. These signals are wave-separated to determine the area ratios, whereby the phosphoric acid condensation composition can be examined.

During the measurement or in the preparation (pretreatment) stage, it is necessary to avoid the contact of the catalyst with moisture. When the catalyst contacts with moisture during the measurement or in the preparation (pretreatment) stage, the condensed phosphoric acid in the catalyst is partially hydrolyzed and changed to orthophosphoric acid. Therefore, accurate measurement cannot be performed.

As the supporting method, it is preferable to dip the carrier in a phosphoric aqueous solution followed by drying, or to mold a paste obtained by mixing a siliceous carrier with the phosphoric acid aqueous solution followed by drying.

The former method is particularly preferred since the phosphoric acid can be properly supplied by redipping the catalyst when the phosphoric acid amount supported is reduced by elution of the phosphoric acid in the catalyst to the reaction solution during dimerization reaction. In the latter method, the same molding method and the same shape of molded product as in the molding of the carrier can be adapted.

For the preparation of the catalyst, the supporting method by dipping the carrier in the phosphoric acid aqueous solution followed by drying will be concretely described. The equipment used for the preparation of the catalyst is not particularly limited, and a general batch tank can be used. By using reactor for carrying out the olefin dimerization reaction, filling of the catalyst can be performed simultaneously with the catalyst preparation. The concentration of the phosphoric acid aqueous solution used for dipping is not particularly limited, but generally set at about 10 to 80 mass %. The concentration can be changed depending on an intended phosphoric acid support amount.

For ensuring a phosphoric acid support amount of 70 mass %, for example, the concentration of the phosphoric acid aqueous solution is generally set to about 35 to 45 mass %, although it varies depending on properties of the carrier such as surface area. The dipping time can be generally set to about 1 hour or more. The dipping temperature is set to lower than 100° C., preferably to not higher than 50° C. A high-temperature condition of 100° C. or higher is not preferred since the proportion of orthophosphoric acid in the phosphoric acid may be low. Further, since an excessively low temperature causes solidification, disabling the dipping, the temperature is preferably set to 0° C. or higher, more preferably, to 15° C. or higher.

After removing the surplus phosphoric acid aqueous solution by a general method such as filtering after dipping, removal of surplus moisture can be appropriately performed by means of evaporation drying, or by standing in the atmosphere or by using a gas flow. As the gas used for drying, any gas which becomes gaseous state in the drying condition can be used without particular limitation, and air, nitrogen gas, hydrogen gas, and C1 to C5 saturated hydrocarbon gases are suitable. The gas may contain a saturated amount or less of water vapor. For example, the drying can be performed at room temperature using air containing 2.5 vol. % or less of water vapor. The drying temperature is set to lower than 100° C., preferably, to not higher than 50° C. At a temperature of 100° C. or higher, the condensation of phosphoric acid is rapidly caused, resulting in reduction in the proportion of orthophosphoric acid in the phosphoric acid, so, not preferable. Since an excessively low temperature deteriorates the drying efficiency, the drying temperature is set preferably to 0° C. or higher, more preferably to 5° C. or higher. The drying time and the flow velocity of the gas are appropriately adjusted so that the proportion of orthophosphoric acid in the phosphoric acid becomes within the above-mentioned range, for example, it is not less than 60 mol % in terms of phosphorus atom amount, while confirming the progress of the condensation of phosphoric acid by drying. The highly-condensed phosphoric acid catalyst with advanced condensation of phosphoric acid can be used by returning it to a low-condensed state (with a proportion of orthophosphoric acid of 60 mol % or more) by redipping treatment.

As the olefin of the olefin-containing raw material, C3 to C7 monoolefins are usable, and straight-chain, branched and cyclic ones can be used alone or in combination according to an intended product. Concrete examples thereof include propylene, butenes (1-butene, cis-2-butene, trans-2-butene, isobutylene), normal pentenes, isopentenes, cyclopentenes, normal hexenes, iso-hexenes, cyclohexenes, normal heptenes, iso-heptenes, cycloheptenes and the like. The dimerization of olefin means that 1 mole of olefin is produced by reaction of 2 moles of a raw material olefin (including, in the case of an olefin-mixed raw material, reactions between different raw material olefins).

In the present invention, as the raw material olefin, for example, butenes are suitably used.

Among the resulting dimers of butenes, isooctene is useful as a high-octane number base material for gasoline production. High-purity diisobutylene is a compound useful as raw materials of functional chemical products such as octyl phenol and isononanoic acid.

In the production of the dimers of butenes, one kind of butenes can be used alone, but a mixture in which several kinds of butenes are mixed in optional ratios is also usable. The composition of the butenes is preferably adjusted according to applications and requested characteristics (octane number, etc.) of the resulting dimerized product. In the range of satisfying the requested characteristics, other olefins, for example, propylene and straight-chain, branched and cyclic pentenes, hexenes, heptenes and the like can be included therein.

The supplying source of the olefin-containing raw material is not particularly limited, and examples thereof include an olefin fraction produced in FCC process, an olefin fraction obtained by removing diene components from fractions produced in a naphtha cracker by extraction or selective hydrogenation, a coker off-gas fraction, a dehydrogenation reaction product or the like, and mixtures obtained by mixing them in optional ratios. These may be further adjusted by increasing and decreasing the content of a specified fraction using known method such as distillation. For example, isobutylene-isobutane fraction containing high concentration of isobutylene which can be obtained by removing normal butenes and normal butane by distillation (or reactive distillation) of FCC-C4 fraction or a raffinate fraction obtained by extracting butadiene from C4 fraction produced in naphtha cracker can be used.

When these fractions are used for dimerization reactions of butenes, they may contain a trace amount of impurity such as butadiene as long as it does not affect the reactions.

For the purpose of removing reaction heat, olefin-containing raw material containing solvent can be used. Any solvent which is liquid in the dimerization reaction condition and substantially inactive to the solid phosphoric catalyst can be used. For example, hydrocarbons such as n-paraffins, isoparaffines, naphthenes and aromatics can be used. Saturated hydrocarbons such as butanes in the raffinate or C4 fraction also act as the solvent. The amount of the solvent is set so that the ratio of olefin to the total amount of the olefin-containing raw materials containing the olefin and the solvent is 1 to 70 mass %, preferably 10 to 65 mass %, and more preferably 15 to 60 mass %. An excessively large amount of the solvent deteriorates the productivity, while an excessively small amount thereof deteriorates the heat removing efficiency.

In the present invention, it is preferable to bring the olefin-containing raw material into contact with the solid phosphoric acid catalyst in a liquid phase. In a gas phase, coking may cause deterioration of the activity and dimer selectivity in olefin dimerization reactions and shortening of the catalyst life.

The reactor and reaction style used for the dimerization reactions of olefin are not particularly limited, batch, semi-batch or continuous flow type reactions by vessel type reactors can be used, also, continuous flow type reactions by fixed bed, fluidized bed, and moving bed flow reactors can be adapted. The reaction temperature is set to 0 to 300° C., preferably to 20 to 200° C. A sufficient reaction rate cannot be ensured at a temperature lower than 0° C., while side reactions are increased at a temperature higher than 300° C. The reaction pressure is preferably set to from an atmospheric pressure to 20 MPa, because the reaction system cannot maintain the liquid phase at a lower pressure, while the facility cost is increased at a higher pressure. WHSV (mass of supplied feed stock per mass of carrier per hour) is set to 0.1 to 300 $hr^{-1}$, preferably to 1 to 150 $hr^{-1}$. The production efficiency is poor with a smaller WHSV, and the reaction does not progress with a larger WHSV.

As described above, although the progress of condensation of orthophosphoric acid is extremely slowed when the proportion of orthophosphoric acid in the phosphoric acid is 60 mol % or more in terms of phosphorus atom amount, the condensation of orthophosphoric acid in the catalyst can gradually proceed with the progress of dimerization reaction depending on the reaction condition.

For preventing the progress of condensation of orthophosphoric acid in the catalyst, it is preferable to make moisture coexist in the reaction system. The method for supplying the moisture is not particularly limited, and a predetermined amount of water can be dissolved in the olefin-containing raw material by a mixing device and supplied to the reactor. The moisture content in the olefin-containing raw material is 10 to 1000 mass ppm, preferably 30 to 500 mass ppm, and more preferably 50 to 300 mass ppm.

When the moisture content is smaller than the above-mentioned range, the frequency of catalyst regeneration is increased since the proportion of orthophosphoric acid in the phosphoric acid in the catalyst is reduced to less than 60 mol % in a relatively short time, resulting in deterioration of the productivity. On the other hand, when the moisture content is larger, excessive moisture (particularly, water of an amount exceeding the saturated moisture amount of the raw material solution) makes the phosphoric acid in the catalyst elute, whereby the activity is undesirably reduced. When the phosphoric acid in the catalyst is reduced by elution in this way, phosphoric acid can be successively added and adequately supplied to the reaction system (catalyst bed).

Example 1

12.0 g of extrusion molded product of diatomite (1.6 mmϕ×2 mm) was dipped in 60 ml of 31-mass % phosphoric acid aqueous solution in a 100-ml beaker. After dipping for 1 hour, the aqueous solution was removed through a mesh filter, standing drying operation was performed in a room with a temperature of 25° C. and a humidity of 50% for 2 hours to prepare a solid phosphoric acid catalyst A. As a result of analysis of phosphorus ($^{31}P$) by solid nuclear magnetic resonance spectrometry for the catalyst, the composition of the phosphoric acid supported (mol % in terms of phosphorus atom amount, hereinafter the same as above) was composed of orthophosphoric acid 85% and pyrophosphoric acid 15% without polyphosphoric acid. As the result of neutralizing titration, the phosphoric acid amount in the catalyst was 20 mass % in terms of orthophosphoric acid amount, and after removing the phosphoric acid by washing of the catalyst with water followed by drying, the ratio of the carrier in the catalyst was 77.5 mass %. Accordingly, the phosphoric acid support amount is 25.8 mass %.

2 g of the solid phosphoric acid catalyst A was packed in a tubular stainless steel reactor (inside diameter: 8 mm), and dimerization reaction was carried out continuously for 30 days while feeding an isobutylene-containing raw material (isobutylene 30 mass %, n-butenes 5 mass %, n-hexane 65 mass %, and water 250 mass ppm) from an upper part of the reactor at a rate of 40 g/h (WHSV=26 $h^{-1}$) and drawing out the reaction product solution from a lower part thereof. A liquid phase state was maintained with a pressure of 1.0 MPa and a catalyst bed temperature of 80° C. The reaction result and the compositions of the phosphoric acid on the catalyst before and after the reaction are shown in Table 1 and in Table 3, respectively.

Example 2

3.0 g of extrusion molded product of diatomite (1 mmϕ×2 mm) was packed in a tubular stainless steel reactor (inside diameter: 8 mm). A 31-mass % phosphoric acid aqueous solution was introduced from the lower part of the reactor just in an amount sufficient to entirely dip the diatomite, and the phosphoric acid aqueous solution was removed from the lower part of the reactor after 1 hour. Drying operation was then carried out by feeding nitrogen gas containing 2 vol. % of moisture from upper part of the reactor at room temperature (25° C.) and a rate of 1 L/H for 90 minutes and discharging it from the lower part. A solid phosphoric acid catalyst B partially taken out of the reactor was analyzed in the same manner as in Example 1. As the result, the phosphoric acid supported had a composition consisting of orthophosphoric acid 87% and pyrophosphoric acid 13% without polyphosphoric acid. The amount of the phosphoric acid (in terms of orthophosphoric acid amount) in the catalyst was 19 mass %, the ratio of the carrier in the catalyst was 77.7 mass %, and the phosphoric acid support amount was thus 24.4 mass %. The amount of the catalyst left in the reactor was 1.86 g.

Then, dimerization reaction was carried out continuously for 30 days while feeding an isobutylene-containing raw material (isobutylene 30 mass %, n-butenes 5 mass %, n-hexane 65 mass %, and water 250 mass ppm) from upper part of the reactor at a rate of 40 g/h (WHSV=28 $h^{-1}$) and drawing out the reaction product solution from the lower part. A liquid phase state was maintained with a pressure of 1.0 MPa and a catalyst bed temperature of 80° C. The reaction result and the compositions of the phosphoric acid on the catalyst before and after the reaction are shown in Table 1 and in Table 3, respectively.

Example 3

Dimerization reaction was carried out in the same manner as in Example 1, except using a raw material composed of isobutylene 35 mass %, n-hexane 65 mass %, and water 250 mass ppm. The reaction result and the compositions of the phosphoric acid on the catalyst before and after the reaction are shown in Table 1 and in Table 3, respectively.

Example 4

Dimerization reaction was carried out in the same manner as in Example 1, except using a raw material composed of isobutylene 8 mass %, n-butenes 27 mass %, n-hexane 65 mass %, and water 250 mass ppm and setting the pressure to 2.0 MPa and the catalyst bed temperature to 145° C. The reaction result and the compositions of the phosphoric acid on the catalyst before and after the reaction are shown in Table 1 and in Table 3, respectively.

Example 5

Dimerization reaction was carried out in the same manner as in Example 1, except using a raw material composed of n-butenes 35 mass %, n-hexane 65 mass % and water 250 mass ppm, and setting the pressure to 2.0 MPa and the catalyst bed temperature to 145° C. The reaction result and the compositions of the phosphoric acid on the catalyst before and after the reaction are shown in Table 1 and in Table 3, respectively.

Example 6

3.0 g of extrusion molded product of diatomite (1 mmϕ×2 mm) was packed in a tubular stainless steel reactor (inside diameter: 8 mm), and a 31-mass % phosphoric acid aqueous solution was introduced from lower part of the reactor just in an amount sufficient to entirely dip the diatomite, and the phosphoric acid aqueous solution was removed from the lower part of the reactor after 1 hour. Drying operation was then carried out by feeding dry nitrogen gas from upper part of the reactor at room temperature (25° C.) and a rate of 1 L/H for 60 minutes and discharging it from the lower part. A solid phosphoric acid catalyst C partially taken out of the reactor was analyzed in the same manner as in Example 1. As the result, the phosphoric acid supported had a composition consisting of orthophosphoric acid 80% and pyrophosphoric acid 20% without polyphosphoric acid. The amount of the phosphoric acid (in terms of orthophosphoric acid amount) in the catalyst was 19 mass %, the ratio of the carrier in the catalyst was 78.3 mass %, and the phosphoric acid support amount was thus 24.3 mass %. The amount of the catalyst left in the reactor was 1.93 g.

Then, dimerization reaction was carried out continuously for 30 days while feeding an isobutylene-containing raw material (isobutylene 30 mass %, n-butenes 5 mass % and n-hexane 65 mass %) which substantially contains no water from an upper part of the reactor at a rate of 40 g/h (WHSV=26 $h^{-1}$) and drawing out from a lower part thereof. A liquid phase state was maintained with a pressure of 1.0 MPa and a catalyst bed temperature of 80° C. The reaction result and the compositions of the phosphoric acid on the catalyst before and after the reaction are shown in Table 1 and in Table 3, respectively.

Example 7

Dimerization reaction was carried out in the same manner as in Example 1, except using a raw material composed of isopentenes 20 mass %, n-pentenes 20 mass %, cyclopentene 10 mass %, n-pentane 50 mass % and water 250 mass ppm, and setting the pressure to 2.0 MPa and the catalyst bed temperature to 145° C. The reaction result and the compositions of the phosphoric acid on the catalyst before and after the reaction are shown in Table 1 and in Table 3, respectively.

Example 8

Dimerization reaction was carried out in the same manner as in Example 1, except using a raw material having a composition consisting of isobutylene 20 mass %, n-butenes 3 mass %, isopentenes 7 mass %, n-pentenes 10 mass %, n-hexane 60 mass % and water 250 mass ppm, and setting the pressure to 1.5 MPa and the catalyst bed temperature to 120° C. The reaction result and the compositions of the phosphoric acid on the catalyst before and after the reaction are shown in Table 1 and in Table 3, respectively.

Comparative Example 1

Same operation as in Example 1 was carried out, except performing the drying operation in a dry oven at 110° C. after removing the phosphoric acid aqueous solution, whereby a solid phosphoric acid catalyst D was prepared. The catalyst was analyzed in the same manner as in Example 1. As the result, the phosphoric acid supported had a composition consisting of orthophosphoric acid 57%, pyrophosphoric acid 38%, and polyphosphoric acid 5%. The amount of the phosphoric acid (in terms of orthophosphoric acid amount) in the catalyst was 20 mass %, the ratio of the carrier in the catalyst was 80.5 mass %, and the phosphoric acid support amount was thus 24.8 mass %. Using the solid phosphoric acid catalyst D, the dimerization reaction was carried out in the same manner as in Example 1. The reaction result and the compositions of the phosphoric acid on the catalyst before and after the reaction are shown in Table 2 and in Table 4, respectively.

Comparative Example 2

Same operation as in Example 2 was performed, except performing, after removing the phosphoric acid aqueous solution, the drying operation by feeding dry nitrogen gas of 200° C. to a supported material prepared by performing dipping in the phosphoric acid aqueous solution and removal of the aqueous solution by the same method as in Example 2 at a rate of 1 L/H for 1 hour from upper part of the reactor (and discharging it from the lower part thereof). A solid phosphoric acid catalyst E taken out of the reactor was analyzed in the same manner as in Example 1. As the result, the phosphoric acid supported had a composition consisting of orthophosphoric acid 25%, pyrophosphoric acid 39% and polyphosphoric acid 36%. The amount of the phosphoric acid (in terms of orthophosphoric acid amount) in the catalyst was 18 mass %, the ratio of the carrier in the catalyst was 83.3 mass %, and the phosphoric acid support amount was thus 21.6 mass %.

Then, using 1.8 g of the catalyst E left in the reactor, dimerization reaction was carried out in the same manner as in Example 2. The reaction result and the compositions of the phosphoric acid on the catalyst before and after the reaction are shown in Table 2 and in Table 4, respectively.

Comparative Example 3

Dimerization reaction was carried out in the same manner as in Comparative Example 1, except using a raw material having a composition consisting of isobutylene 35 mass %, n-hexane 65 mass % and water 250 mass ppm. The reaction result and the compositions of the phosphoric acid on the catalyst before and after the reaction are shown in Table 2 and in Table 4, respectively.

Comparative Example 4

Dimerization reaction was carried out in the same manner as in Comparative Example 1, except using a raw material having a composition consisting of isobutylene 8 mass %, n-butenes 27 mass %, n-hexane 65 mass % and water 250 mass ppm, and setting the pressure to 2.0 MPa and the catalyst bed temperature to 145° C. The reaction result and the compositions of the phosphoric acid on the catalyst before and after the reaction are shown in Table 2 and in Table 4, respectively.

Comparative Example 5

Dimerization reaction was carried out in the same manner as in Comparative Example 2, except using a raw material having a composition consisting of n-butenes 35 mass %, n-hexane 65 mass % and water 250 mass ppm, and setting the pressure to 2.0 MPa and the catalyst bed temperature to 145° C. Since no dimerized product was obtained, the reaction was terminated in 5 hours. The reaction result and the composition of phosphoric acid on the catalyst before the reaction are shown in Table 2 and in Table 4, respectively.

TABLE 1

Reaction Result

| | | Example | | | | | | | |
|---|---|---|---|---|---|---|---|---|---|
| | | 1 | 2 | 3 | 4 | 5 | 6 | 7 | 8 |
| After 5 hrs | Olefin Conversion (%) | 75 | 76 | 80 | 48 | 35 | 76 | 48 | 71 |
| | Dimer Selectivity (%) | 90 | 89 | 80 | 93 | 94 | 90 | 92 | 88 |
| | Dimer Yield (%) | 68 | 68 | 64 | 45 | 33 | 68 | 44 | 62 |
| After 30 days | Olefin Conversion (%) | 80 | 80 | 86 | 50 | 37 | 57 | 41 | 75 |
| | Dimer Selectivity (%) | 85 | 88 | 75 | 93 | 93 | 85 | 91 | 85 |
| | Dimer Yield (%) | 68 | 70 | 65 | 47 | 34 | 48 | 46 | 64 |

TABLE 2

Reaction Result

| | | Comparative Example | | | | |
|---|---|---|---|---|---|---|
| | | 1 | 2 | 3 | 4 | 5 |
| After 5 hrs | Olefin Conversion (%) | 49 | 32 | 55 | 41 | 0 |
| | Dimer Selectivity (%) | 85 | 64 | 77 | 87 | — |
| | Dimer Yield (%) | 42 | 20 | 42 | 36 | 0 |
| After 30 days | Olefin Conversion (%) | 40 | 22 | 41 | 21 | — |
| | Dimer Selectivity (%) | 67 | 50 | 63 | 75 | — |
| | Dimer Yield (%) | 27 | 11 | 26 | 16 | — |

TABLE 3

Phosphoric acid Composition in Catalyst Before and After Reaction

| | | Example | | | | | | | |
|---|---|---|---|---|---|---|---|---|---|
| | | 1 | 2 | 3 | 4 | 5 | 6 | 7 | 8 |
| Before reaction | Orthophosphoric acid | 85 | 87 | 85 | 85 | 85 | 80 | 85 | 85 |
| | Pyrophosphoric acid | 15 | 13 | 15 | 15 | 15 | 20 | 15 | 15 |
| | Polyphosphoric acid | 0 | 0 | 0 | 0 | 0 | 0 | 0 | 0 |
| After 30 days | Orthophosphoric acid | 79 | 82 | 81 | 79 | 77 | 59 | 78 | 80 |
| | Pyrophosphoric acid | 21 | 18 | 19 | 21 | 22 | 36 | 22 | 20 |
| | Polyphosphoric acid | 0 | 0 | 0 | 0 | 1 | 5 | 0 | 0 |

(mol % in terms of phosphorus atom amount)

TABLE 4

Phosphoric acid Composition in Catalyst Before and After Reaction

| | | Comparative Example | | | | |
|---|---|---|---|---|---|---|
| | | 1 | 2 | 3 | 4 | 5 |
| Before reaction | Orthophosphoric acid | 57 | 25 | 57 | 57 | 26 |
| | Pyrophosphoric acid | 38 | 39 | 38 | 38 | 40 |
| | Polyphosphoric acid | 5 | 36 | 5 | 5 | 34 |
| After 30 days | Orthophosphoric acid | 42 | 13 | 35 | 45 | — |
| | Pyrophosphoric acid | 46 | 31 | 45 | 47 | — |
| | Polyphosphoric acid | 12 | 56 | 20 | 8 | — |

(mol % in terms of phosphorus atom amount)

INDUSTRIAL APPLICABILITY

The solid phosphoric acid catalyst of the present invention can be used in various reactions using acid catalyst such as hydration reaction of olefin, alkylation reaction of aromatic compounds besides the olefin dimerization.

The invention claimed is:

1. A solid phosphoric acid catalyst, comprising phosphoric acid, a compound that forms phosphoric acid by hydrolysis, or a mixture of both, supported on a carrier, the proportion of orthophosphoric acid in the phosphoric acid, compound, or mixture supported being 60 mol % or more in terms of phosphorus atom amount, wherein the catalyst is prepared by bringing a phosphoric acid aqueous solution into contact with the carrier followed by drying, the preparation process being performed at a temperature lower than 100° C.

2. A method for dimerization of olefin, comprising bringing an olefin-containing raw material into contact with the solid phosphoric acid catalyst according to claim 1.

3. The method according to claim 2, wherein the olefin-containing raw material contains water in an amount of 10 to 1000 mass ppm.

4. The method according to claim 2, wherein the olefin-containing raw material is brought into contact with the solid phosphoric acid catalyst in liquid phase.

5. The method according to claim 2, wherein the olefin is a monoolefin having 3 to 7 carbon atoms or mixture of those monoolefins.

6. A method for dimerization of olefin, comprising bringing an olefin-containing raw material into contact with the solid phosphoric acid catalyst according to claim 1,
wherein the olefin-containing raw material contains water in an amount of 10 to 1000 mass ppm
wherein the olefin-containing raw material is brought into contact with the solid phosphoric acid catalyst in liquid phase;
wherein the olefin is a monoolefin having 3 to 7 carbon atoms or mixture of those monoolefins.

7. The catalyst of claim 1, wherein the proportion of orthophosphoric acid is 70 mol % or more in terms of phosphorus atom amount.

8. The catalyst of claim 7, wherein the proportion of orthophosphoric acid is 80 mol % or more in terms of phosphorus atom amount.

9. The method according to claim 2, wherein the proportion of orthophosphoric acid in the catalyst is 70 mol % or more in terms of phosphorus atom amount.

10. The method according to claim 2, wherein the proportion of orthophosphoric acid in the catalyst is 80 mol % or more in terms of phosphorus atom amount.

* * * * *